United States Patent [19]

Archer

[11] Patent Number: 4,851,417

[45] Date of Patent: Jul. 25, 1989

[54] 9-SUBSTITUTED 6H-PYRIDO[4,3-B]CARBAZOLES

[75] Inventor: Sydney Archer, Delmar, N.Y.

[73] Assignee: Rensselaer Polytechnic Institute, Troy, N.Y.

[21] Appl. No.: 198,976

[22] Filed: May 26, 1988

[51] Int. Cl.$^4$ .................. A61K 31/475; C07D 471/04
[52] U.S. Cl. ........................................ 514/285; 546/70
[58] Field of Search .......................... 546/70; 514/285

Primary Examiner—Donald G. Daus
Assistant Examiner—Andrew G. Rozycki
Attorney, Agent, or Firm—Notaro & Michalos

[57] ABSTRACT

Compounds comprising the series of 9-substituted 5-hydroxymethyl-11-methyl-6H-pyrido[4,3-b]carbazole N-alkyl or aryl carbamates of general structure:

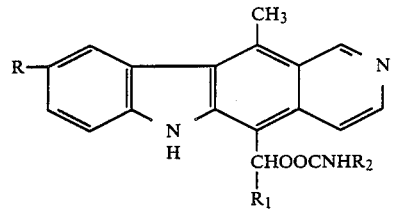

where R=H, lower alkoxy, OH, aryloxy
$R_1$=H or lower alkyl
$R_2$=lower alkyl or aryl.

7 Claims, No Drawings

9-SUBSTITUTED 6H-PYRIDO[4,3-B]CARBAZOLES

STATEMENT OF GOVERNMENT INTEREST

This invention resulted from research sponsored by the National Cancer Institute under grant no. R01-CA19674. The government has an interest in this application.

FIELD AND BACKGROUND OF THE INVENTION

The present invention relates in general to ellipticine-like chemicals which have been shown to have schistosomicidal and antitumor effects, and in particular 9-substituted 5-hydroxymethyl-11-methyl-6H-pyrido [4,3-b] carbazole N-alkyl or aryl carbamates.

A great deal of interest has been shown in the alkaloids ellipticine (1; 5,11-dimethyl-6H-pyrido [4,3-b] carbazole) and its regioisomer olivacine (2; 1,5-dimethyl-6H-pyrido [4, 3-b] carbazole) because of their antitumor properties in animals and humans. Ellipticine has been shown to react with DNA by an intercalation process which may account for its cytotoxicity. It has also been found that 1 markedly inhibited DNA polymerase but not RNA polymerase. At concentrations of 0.2 and 1.0 micrograms/mL, the drug inhibited DNA and RNA synthesis as measured by the incorporation of [$^3$H]thymidine and [$^3$H]uridine. At these concentrations there was little effect on protein synthesis. It was concluded that inhibition of nucleic acid synthesis was an important contribution to the cytotoxic effect of ellipticine. See: Suffness, M.; Cardell, G.A. *The Alkaloids*; Brossi, A., Ed.; Academic: New York, 1985; Vol. XXV; LePecq, J-B.; Dat Xoung, N.; Gosse, C.; Paoletti, C. *Proc. Natl. Acad. Sci.* U.S.A. 1974, 71, 5078. Maftouh, M.; Bessielievre, Monserrat, B.; Lesca, P.; Meunier, B.; Husson, H.P.; Paoletti, C. *J. Med. Chem.* 1985, 28, 708; and Li, L.M.; Cowie, C.H. *Biochem. Biophys.* Acta 1974, 353, 3751.

One author (Sethi, V.S. *Biochem. Pharmacol.* 1981, 30, 2026) was able to show that 1 did inhibit RNA polymerase but at concentrations far higher than those of other antitumor agents such as dactinomycin, adriamycin, and daunomycin.

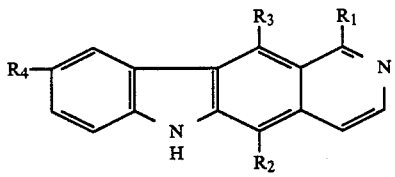

1 (ellipticine): $R_1 = R_4 = H$, $R_2 = R_3 = CH_3$ 2 (olivacine): $R_1 = R_2 = CH_3$, $R_3 = R_4 = H$ 3 (9-hydroxyellipticine): $R_1 = H$, $R_2 = R_3 = CH_3$, $R_4 = OH$

4: $R_1 = R_3 = R_4 = H$, $R_2 = CH_3$

5: $R_1 = R_2 = R_3 = R_4 = H$

6: $R_1 = R_2 = CH_3$, $R_3 = H$, $R_4 = OH$

7: $R_1 = R_3 = H$, $R_2 = CH_3$, $R_4 = OH$

Compound 3 was found to produce DNA double and single strand breaks in L1210 cells exposed to the drug, and that this compound was a more active antitumor agent than 1. Compounds 2 and 4 were also found to be active antitumor agents in vivo. Compound 6 was found to be cytotoxic. Compound 7 was found to be inactive in vivo against murine L1210 leukemia. Compound 5 was also found to be inactive.

In other studies on the mode of antischistosomal and antitumor action of lucanthone (8) and hycanthone (9) and its cogeners, evidence was found that the methyl group of lucanthone (8) is metabolized in the mammalian host to hycanthone (9), which then may be enzymically esterified to either 10 or 11. These may dissociate nonenzymically to the carbonium ion 12, which alkylates DNA to form the adduct 13. The carbamate ester 14 acted as a surrogate for 10 or 11. The enhanced antitumor action of 15, in which the 7-OH is regiochemically analogous to the 9-OH in 6, was attributed to stronger intercalation into DNA as compared with hycanthone. See: Archer, S.; Yarinsky, A. *Prog. Drug. Res.* 1972, 16, 12; Cioli, D.; Pica-Mattoccia, L.; Rosenburg, S.; Archer, S. *Life Sci.* 1985, 37, 161; Archer, S.; Zayed, A. H; Rej, R.; Rugino, T.A. *J. Med. Chem.* 1983, 26, 1240; and U.S. Pat. No. 4,539,412 to Archer.

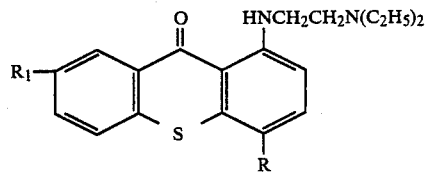

8 (lucanthone): $R = CH_3$, $R_1 = H$ 9 (hycanthone): $R = CH_2OH$, $R_1 = H$

10: $R = CH_2OPO_3H^-$, $R_1 = H$

11: $R = CH_2OSO_3^-$, $R_1 = H$

12: $R = CH_2^+$, $R^1 = H$

13: $R = CH_2-DNA$, $R_1 = H$

14: $R = CH_2OOCNHCH_3$, $R_1 = H$

15: $R = CH_2OH$, $R_1 = OH$

In view of the foregoing results, the role of the methyl groups in the ellipticine series is believed to be very important. One hypothesis to rationalize the lack of activity of compound 5 is that the lack of a C-5 methyl group does not permit the metabolic conversion of a hydroxymethyl group, which on enzymic esterification would be converted to an alkylating agent similar to compounds 10 and 11.

SUMMARY OF THE INVENTION

To examine the hypothesis that metabolic conversion of the 5-methyl group would lead to covalent binding to DNA, 5-(hydroxymethyl)-11-methyl-6H-pyrido [4,3-b] carbazole (25) and its N-methyl-carbamate (27) were synthesized and the effect of these drugs on DNA synthesis in HeLa cells and their antitumor activity in murine P388 lymphocytic leukemia were studied.

Experimental results demonstrate that in fact compound 27 does have significant antitumor activity which, in all cases, is better than the activity of ellipticine (1) or 25.

The compounds of the present invention are active in several antitumor systems, especially a lung tumor line which is refractory to most antitumor drugs. Compound 27 in all cases is far more active than ellipticine, to which the inventive compound is related, to adriamycin, a clinically proven antitumor drug, and to compound 25. Furthermore, compound 27 was found to be schistosomicidal in both hycanthone-sensitive and hycanthone-resistant worms whereas compounds 1 and 25 were not.

An object of the present invention thus is to provide new and useful compounds comprising a series of 9-substituted 5-hydroxymethyl-11-methyl-6H-pyrido [4,3-b] carbazole N-alkyl or aryl carbamates of general structure:

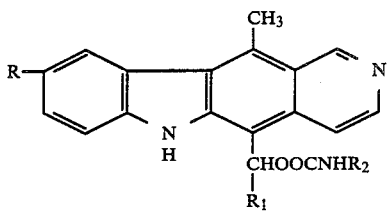

where R=H, lower alkoxy, OH, aryloxy
$R_1$=H or lower alkyl
$R_2$=lower alkyl or aryl which possess outstanding antitumor activity in mice and cell cultures and are active against schistosomidsis.

Lower alkoxy and lower alkyl, as used above, is meant to signify radicals having from 1 to 5 carbon atoms.

DESCRIPTION OF THE PREFERRED EMBODIMENTS

Compound 27, as shown in Scheme I, has been found particularly active as an antitumor agent.

The preparation of 5-(hydroxymethyl)-11-methyl-6H-pyrido [4,3-b] carbazole (25, a precursor of 27) was accomplished by using a modification of the Weller synthesis of ellipticine (Weller, D.D.; Ford, D.W. Tetrahedron Lett. 1984, 25, 2104) as shown in Scheme I.

Scheme I

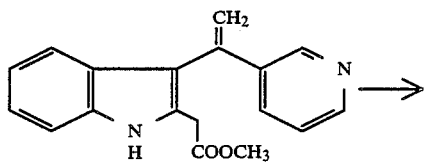

16

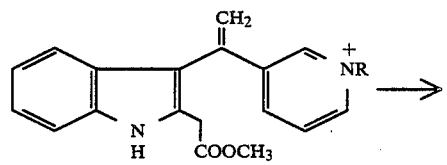

17: R = CH₃
18: R = CH₂C₆H₅
19: R = CH₂C₆H₄—p-NO₂

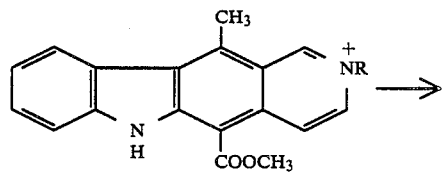

20: R = CH₃
21: R = CH₂C₆H₅
22: R = CH₂C₆H₄—p-NO₂

-continued

![structure 23]

23

![structure 25-27]

25: R = CH₂OH
26: R = CHO
27: R = CH₂OOCNHCH₃

![structure 24]

24

Acid-catalyzed condensation of methyl indole-2-acetate, with 3-acetylpyridine, furnished the vinylindole 16. This was converted to the quaternary ammonium salts 17–19 with the appropriate halides. Cyclization in methanol containing sodium methoxide, followed by treatment with a quaternary salt of ethyl nicotinate resulted in ring closure and aromatization to afford 20–22. Heating either 20 or 21 with a number of nucleophiles (e.g., thiophenoxide ion) did not furnish the required ester 23 in usable yield. Catalytic hydrogenation of 21 gave 23 in very low yields; the major product contained a reduced pyridine ring with the benzyl group still attached to the nitrogen. Treatment of 22 with nitrosodimethylaniline, as described by Kröhnke (Kröhnke, F. Chem. Ber1938, 71, 2583) to give the nitrone 24 and the desired ester 23 in 47% yield, accompanied by a red by-product, which was difficult to remove chromatographically. Reduction of the crude ester with LAH gave the required alcohol 25 in greater than 50% yield for the two steps. Oxidation of 25 with MnO₂ gave the aldehyde 26, a natural product whose synthesis was reported recently by Gribble (Saulnier, M.; Gribble, G. Tetrahedron Lett. 1983, 24, 3831). Direct comparison of the infrared spectrum of 26 with the natural alkaloid showed that the spectra were identical. Treatment of 25 with methyl isocyanate afforded the carbamate 27.

Ellipticine (1), 5-(hydroxymethyl)-11-methyl-6H-pyrido [4,3-b] carbazole (25), and its corresponding N-methylcarbamate (27) were tested for antitumor activity at the Lederle Laboratories. The results are summarized in Table I.

TABLE I

| Activity against P388 Lymphocytic Leudemia of Ellipticine, 5-(Hydroxymethyl)-11-methyl-6H—pyridol[4,3-b]carbazole, and Ita Carbamate in Mice[a] | | | |
|---|---|---|---|
| compound | dose | MST[b] | % ILS[c] |
| placebo | | 10 | control |
| ellipticine (l) | 40 | 16.0 | 60 |
| | 20 | 13.0 | 30 |

TABLE I-continued

Activity against P388 Lymphocytic Leudemia of Ellipticine, 5-(Hydroxymethyl)-11-methyl-6H—pyridol[4,3-b]carbazole, and Ita Carbamate in Mice[a]

| compound | dose | MST[b] | % ILS[c] |
|---|---|---|---|
|  | 10 | 13.0 | 30 |
|  | 5 | 12.0 | 20 |
| 25 |  |  |  |
|  | 80. | 18 | 80 |
|  | 40. | 16.5 | 65 |
|  | 20. | 16.5 | 65 |
|  | 10 | 14.5 | 45 |
|  | 5 | 13 | 30 |
|  | 2.5 | 12.5 | 25 |
| 27 |  |  |  |
|  | 80. | 6.0 | toxic |
|  | 40. | 10.0 | 0 |
|  | 20. | 15.0 | 50 |
|  | 10 | 21.0 | 110 |
|  | 5 | 16.0 | 60 |
|  | 2.5 | 18.0 | 80 |

[a]The compounds were administered ip on days 1,5 and 9 in a 9-day protocol at Lederle Laboratories.
BDFR-1 mice were inoculated ip with $10^6$ P388 cells at day 0.
[b]MST = median survival time.
[c]% ILS = percent increase in life span relative to controls.

TABLE II

Effect of Ellipticine, 5-(Hydroxymethyl)-11-methyl-6H-pyrido[4,3-b]carbazole, and Its Carbamate on [³H]Thymidine Incorporation by HeLa Cells[a]

| compound | concn, µg/mL | % incorporation of [³H]thymidine compared to control | |
|---|---|---|---|
| | | in presence of drug | 3 h after washing |
| ellipticine | 5 | 65 | 78 |
|  | 10 | 56 | 47 |
|  | 25 | 8 | 25 |
| 25 | 5 | 67 | 88 |
|  | 25 | 22 | 52 |
| 27 | 5 | 59 | 18 |
|  | 25 | 27 | 3 |

[a]The drugs 1, 25, and 27 were added to growing cultures of HeLa cells and 1 h later [³H]thymidine was added. After another 1 h the amount of the labeled base incorporated by the cells was determined. In another experiment HeLa cells were exposed to the drugs for 1 h and then washed thoroughly. Three hours later [³H]thymidine was added and the above procedure was repeated.

Ellipticine and the carbinol 25 were about equipotent, but the carbamate 27 was more active than either. The latter exhibited significant antitumor activity at a dose of 2.5 mg/kg and was toxic at the 80 mg/kg dose level. The effect of these drugs on [³H]thymidine incorporation in HeLa cells is summarized in Table II.

Ellipticine and the carbinol 25 blocked [³H]thymidine incorporation, but the inhibition was partially reversible 3 hours after washing. The carbamate 27 blocked [³H]thymidine incorporation also, but in this instance the blockade was irreversible. Compound 27 blocked uridine and thymidine uptake in schistosomes and was more active than either ellipticine 1 and compound 25. This result is similar to that obtained with hycanthone (9) and its carbamate 14 in schistosomes and HeLa cells. Hycanthone blocked incorporation of [³H]uridine, but, after washing, incorporation resumed, whereas the carbamate 14 was effective in preventing [³H]uridine incorporation in washed and unwashed cells.

On the basis of this evidence, an alternate mechanism is proposed (Scheme II) to account for the antitumor activity of ellipticine and some of its active congeners.

Ellipticine is metabolically converted to 9-hydroxyellipticine (3), a known metabolite of 1, (Rheinhold, V.; Bittman, L.; Bruni, R.; Thrun, K.; Silveria, D. Proc. Am. Assoc. Cancer Res. 1975, 16 135 and Lesca, P.; Lecointe, P.; Paoletti, C.; Mansuy, D.C.R. Acad. Sci., Ser. D 1976, 282, 1457). This species, in turn, is enzymatically converted first to the carbinol 28, which then is transformed enzymatically to 29. This compound, which now possesses a good leaving group, alkylates a nucleophilic macromolecule such as DNA or possibly topoisomerase II to give 30. The carbamate 27 acts as a surrogate for 30 just as hycanthone N-methylcarbamate (14) does for the corresponding phosphate 10 or sulfate 11.

Such a mechanism can account for the greater antitumor potency and toxicity of 27 if it assumed that the observed irreversible binding in HeLa cells is due to alkylation of a macromolecule.

One author (Ross, W.E. Biochem. Pharmacol. 1985, 34, 4191) has pointed out that ellipticine causes a higher frequency of DNA strand breaks than adriamycin, yet it is far less cytotoxic. He suggests that ellipticine induced breaks are rapidly repaired when the drug is removed from the surrounding medium whereas the adriamycin-induced breaks are retained much longer. If the carbamate 27 forms covalent bonds with macromolecules as in 30, it should be retained much longer than ellipticine or the carbinol 25, consequently, repair should occur more slowly, if at all and thus is more active than adriamycin.

Scheme II $1 \longrightarrow 3 \longrightarrow$

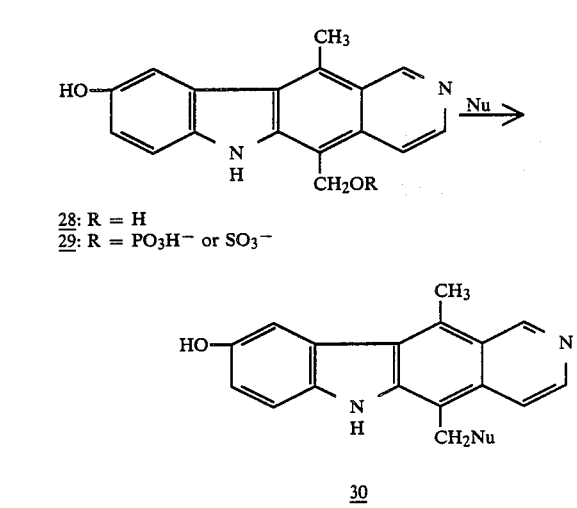

28: R = H
29: R = $PO_3H^-$ or $SO_3^-$

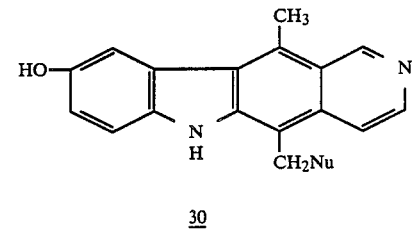

30

Additional tests comparing the activity of adriamycin, ellipticine, compounds 25 and 27 have been conducted, and demonstrate the superiority of compound 27. The results of these experiments are shown in Table III.

Tests have also been conducted which confirm the activity of compound 27 against schistosomiasis (a type of worm).

Synethetic index as % of control

|  | ³H—uridine | | ¹⁴C—uridine | | ³H—thymidine | |
|---|---|---|---|---|---|---|
|  | Sens. | Res. | Sens. | Res. | Sens. | Res. |
| Ellipticine |  |  | 100 | 100 | 100 | 77 |
| 25 | 100 | 70 | 92 | 100 | 44 | 40 |
| 27 | 18 | 18 | 56 | 47 | 25 | 27 |

In vitro survival on the 30th day of culture:

|  | Sensitive | Resistant |
| --- | --- | --- |
| Ellipticine | all alive | all alive |
| 25 | all alive | all alive |
| 27 | 4 dead/6 | 3 dead/6 |

S. mansoni adult male worms were exposed for 1 hour in vitro to 50 micrograms/ml of the drug (some drug re-precipitated in the medium), washed and incubated overnight in drug-free medium. At the end of overnight incubation, the radioactive precursor was added for 1 hour and the trichloroacetic acid-soluble and trichloroacetic acid-precipitable radioactivity associated with schistosomes was determined. Synthetic index was calculated according to Pica-Mattoccia & Cioli (Mol. Biochem. Parasitol. 8:99, 1983). Values represent the synthetic index expressed as a % of the control untreated schistosomes.

TABLE III
Percent Survival of Various Lung Cancer Cell Lines After One Hour Exposure to Drugs Followed by Washing

| Compound | Conc. ($\mu$mol) | Cell Line | | | |
| --- | --- | --- | --- | --- | --- |
|  |  | H—69* | N-417 | H-460 | H-358 |
| Adriamycin | 0.22 | 95.7 | 86.5 | 51.0 | 66.5 |
|  | 2.2 | 50.5 | 80.3 | 27.0 | 41.5 |
|  | 22 | 14.5 | 39.0 | 0.8 | 0.9 |
| Ellipticine (1) | 0.0033 | 100 | 94.6 | 73.1 | 54.4 |
|  | 0.033 | 43 | 1.9 | 0.8 | 10.6 |
|  | 0.33 | 9.7 | 0 | 0.2 | 0 |
| Compound 25 | 0.0033 | 92.5 | 109.3 | 94.5 | 92.7 |
|  | 0.33 | 39.6 | 40.7 | 18.9 | 53.2 |
|  | 0.33 | 16.5 | 9.1 | 0.6 | 13.1 |
| Compound 27 | 0.0033 | 52.9 | 25.1 | 10.1 | 27.0 |
|  | 0.033 | 31.6 | 4.2 | 0.6 | 0 |
|  | 0.33 | 16.2 | 3.5 | 0 | 0 |

*H-69  Small cell (Generally refractory)          3  Rank of
H-417  Variant small cell (Generally sensitive)   2  Order of
H-460  Non-small cell (Generally responsive)      1  Sensitivity
H-358  Non-small cell (Refractory)                4  Drugs Synthesis of 5-hydroxymethyl-11-methyl-6H-pyrido [4,3-b] carbazole N-methylcarbamate (27)

1-[2-(Carbomethoxymethyl)-3-indolyl]-1-(3-pyridyl) ethene (16)

A solution of 6.13 g (0.032 m) of methyl indole-2 acetate, 7.16 g (7.0 mL, 0.059 m) of 3-acetylpyridine, and 10 mL of concentrated $H_2SO_4$ in 200 mL of dry MeOH was refluxed for 2 hours in an atmosphere of $N_2$. The clear red solution was poured onto 600 g of ice. It was made alkaline with $NH_4OH$ and extracted with $2\times500$ mL portions of ether. The ether solution was washed with $H_2O$, dried, and concentrated to dryness. The residue was triturated with hexane-ether (1:1), and the crystals that formed were collected and dried; wt 8.0 g; mp 154°–157° C. (lit. mp 160°–161° C.). The material was suitable for the next step. An additional 110 mg separated from the ether-hexane filtrate. Total yield 8.17 g.

2-(p-Nitrobenzyl)-5-carbomethoxy-11-methyl-6H-pyrido [4,3-b] carbazolium Bromide (22)

Three grams (0.01 mol) of the ester 16 and 12.0 g (0.05 mol) of p-nitrobenzyl bromide in 140 mL of reagent grade acetone was stirred for 24 h. The crystals of 19 were collected, washed with ether, and dried; wt 4.72 g (92%). To a solution of 150 mg of metallic sodium in 40 mL of dry MeOH there were added 2.67 g (5.25 mmol) of crude 19 and 4.52 g (18.4 mmol) of ethyl nicotinate methobromide. The solution was stirred for 22 hours at room temperature in a nitrogen atmosphere. The crystallize solid that separated was filtered, washed with methanol, and dried; wt 2.31 g (80%) of the desired p-nitrobenzyl quaternary salt 22. The analytical sample was obtained by crystallization from $CH_2Cl_2$-MeOH (1:1): mp 284°–289° C. dec; NMR ($Me_2SO$-$d_6$) $\delta$12.13 (s, 1 H), 10.40 (s, 1 H), 9.31 (d, 1 H), 8.69 (d, 1 H), 8.49 (d, 1 H), 8.33 (d, 2 H), 7.86 (m, 3 H), 7.7–7.65 (m, 1 H), 7.50–7.47 (m, 1 H), 6.20 (s, 2 H), 4.13 (s, 3 H), 3.41 (s, 3 H); IR (KBr) 3240, 3045, 2945, 1717, 1590, 1420 cm$^{-1}$.

5-Carbomethoxy-11-methyl-6H-pyrido [4,3-b] carbazole (23)

To a solution of 200 mg (13 mmol) of metallic sodium in 600 mL of dry MeOH there were added 2.70 g (5.3 mmol) of the quaternary salt 22, 1.06 g (6.3 mmol) of p-nitrosodimethylaniline, and 300 mL of dry $CHCl_3$. The suspension was stirred overnight at room temperature in a nitrogen atmosphere and then evaporated to dryness. The residue was suspended in a solution of 30 mL of $CHCl_3$ and 5 mL of MeOH and flash chromatographed on a column of 40 g of silica gel with ether-triethylamine (20:1) as the eluant. The purest fraction was set aside and the less pure material was rechromatographed. The process was repeated, and the purest fractions which showed essentially only one spot on TLC were combined; wt 715 mg (47%). After crystallization from EtOAc-$CH_2Cl_2$ (5:1), the yellow needles melted at 203°–204° C. dec: NMR ($Me_2SO$-$d_6$) 11.56 (s, 1 H), 9.73 (s, 1 H), 8.87 (d, 1 H), 8.53 (d, 1 H), 8.38 (d, 1 H), 7.80 (d, 1 H), 7.60–7.52 (m, 1 H), 7.30–7.29 (m, 1 H), 4.10 (s, 3 H), 3.33 (s, 3 H); IR (KBr) 3300, 2950, 1675, 1600, 1465 cm$^{-1}$.

5-(Hydroxymethyl)-11-methyl-6H-pyrido [4,3-b] carbazole (25)

A solution of 170 mg (0.74 mmol) of metallic sodium in 150 mL of MeOH, 1.78 g (3.5 mmol) of the quaternary salt 22, 581 mg (3.5 mmol) of p-nitrosodimethylaniline, and 75 mL of dry $CHCl_3$ was stirred for 5 hours at room temperature in an atmosphere of $N_2$. The suspension was evaporated to dryness and the dried residue was dissolved in 100 mL of dry THF. To the resulting solution there was added 300 mg of LAH. After the mixture was stirred for 1 hour at room temperature, 600 mg of LAH was added. After 20 min the reaction was judged to be complete (TLC). The mixture was worked up in the usual way, and the solid that was collected was washed thoroughly with five portions of hot $CH_2Cl_2$-MeOH (1:1). The aqueous filtrate was extracted with $3\times200$ mL portions of $CH_2Cl_2$. The combined organic layers were concentrated to dryness, and the residue was suspended in 30 mL of $CH_2Cl_2$ and 5 mL of MeOH. The suspension was flash chromatographed on silica gel, first with EtOAc as the eluant and then with EtOAc-MeOH (5:1). The purest fractions were combined, concentrated to a small volume, and cooled, whereupon the desired carbinol crystallized to give 518 mg (56% for the two steps) of 25, which melted at 257°–258° C. dec after one crystallization from EtOAc-MeOH (5:1): NMR ($Me_2SO$-$d_6$) $\delta$11.46 (s, 1 H), 9.71 (s, 1 H), 8.43 (d, 1 H), 8.39 (d 1 H), 8.08 (d, 1 H), 7.62–7.48 (m, 2 H), 7.30–7.22 (m, 1 H), 5.25 (s, 3 H), 3:32 (s, 3 H).

5-Formyl-11-methyl-6H-pyrido [4, 3-b] carbazole (17-Oxoellipticine) (26)

A suspension of 40 mg of the carbinol 25 and 200 mg of $MnO_2$ in 35 mL of $CHCl_3$ was heated under reflux for 3.5 h. The hot suspension was filtered and the collected solid was washed with $CHCl_3$. The combined filtrates were evaporated to dryness to leave a residue, which was chromatographed on silica gel. Elution with EtOAc furnished 23 mg of the desired aldehyde 27, which melted at 274°–276° C. (lit mp 275°–276° C.) after crystallization from $CHCl_3$-hexane. The IR spectrum was identical in all respects with that of an authentic sample. Further elution of the column with EtOAc-MeOH (19:1) gave 11 mg of recovered starting material.

5-(Hydroxymethyl)-11-methyl-6H-pyrido [4,3-b] carbazole N-Methylcarbamate (27)

To a solution of 400 mg (1.53 mmol) of the carbinol 25 in 25 mL of dry pyridine and 20 mL of reagent grade acetone there was added 900 uL of MeNCO. The solution was magnetically stirred at room temperature in a stoppered flask until all the starting alcohol had disappeared as judged by TLC (ca. 3 days). The solvents were removed in vacuo, and the residue was crystallized from $EtOAc-CH_2Cl_2$-MeOH to give 152 mg of the desired carbamate, mp 213°–214.5° C. The filtrate was concentrated to dryness and the remaining solid was flash chromatographed to give an additional 145 mg of material of similar purity: wt 307 mg (61%); NMR ($Me_2SO-d_6$) 11.62 (s, 1 H), 9.71 (s, 1 H), 8.46 (d, 1 H), 839 (d, 1 H), 7.97 (d, 1 H), 7.61–7.54 (m, 2 H), 7.32–7.29 (m, 1 H), 7.04 (d, 1 H), 5.77 (s, 2 H), 3.34 (s, 3 H), 2.60 (s, 3 H).

In a similar fashion treatment of 27 with ethyl isocyanate, n-propyl isocyanate, isopropyl isocyanate, butyl isocyanate, t-butyl isocyanate, amyl isocyanate and phenyl isocyanate gave 28

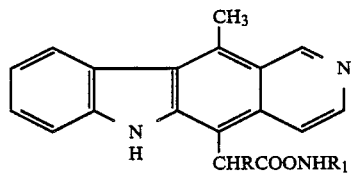

where R=H and $R^1$= ethyl, propyl, isopropyl, n-butyl, t-butyl, n-amyl and phenyl, respectively.

Preparation of 5-hydroxyethyl-11-methyl-6H-pyrido [4,3-b] carbazole N-methyl carbamate (31, R=$CH_3$, $R_1$=$CH_3$)

A solution of the aldehyde 26 in dry ethyl ether was stirred and cooled in an ice-bath as a solution of methylmagnesium iodide in dry ethyl ether was added slowly. After all the Gregnard reagent was added, the mixture was stirred at room temperature and then poured carefully onto ice-water. The ether layer was separated, washed with $NaHCO_3$ solution and evaporated to dryness. The residue was chromatographed on a silica gel column and the desired 5-hydroxyethyl-11-methyl 6H-pyrido [4, 3-b] carbazole was collected and dissolved in a solution of dry pyridine and dry acetone. Excess methyl isocyanate was added and the reaction mixture was stirred until the alcohol was completely consumed as judged by thin-layer chromatography. The solvents were removed in in vacuo and the described compound was purified by crystallization from ethyl acetate - methylene chloride.

The preparation of 9-methoxy-5-hydroxymethyl-11-methyl-6H-pyrido [4, 3-b] carbazole N-methyl carbamate 37 and the corresponding 9-hydroxy compound 43 were prepared as shown in Scheme III.

Methyl 5-methoxy indole-2-carboxylate (32)

Six grams of 5-methoxy indole-2-acetonitrile was dissolved in 60 mL of methanol and the solution was cooled in an ice-bath while dry HCl gas was bubbled into the solution. After 30 minutes the mixture was heated to 40°–45° C. while the HCl was still being added for an additional 3 hours. The flask was stoppered and allowed to stand at room temperature overnight. The next day most of the the methanol was removed in vacuo and the residue was dissolved in ether. The ether solution was thoroughly washed with water, $NaHCO_3$ solution and again with water. The dried ether extract was taken to dryness and the residue was chromatographed on silica gel using ethylacetate/hexane as the developing solvent. There was obtained 6.0 g of the desired methyl ester, m.p. 94°–95° C. after crystallization from benzenehexane.

1-[2-Carbomethoxymethyl-5-methoxy-3-indolyl]-1-(3-pyridyl ethene (33)

To a solution of the ester 32 (5.5 g) and 9.5 mL of 3-acetylpyridine there was added carefully 12 mL of conc. sulfuric acid and the resulting solution was refluxed gently for 2 hours in an atmosphere of nitrogen and allowed to stand at room temperature for an additional 5 hours. The mixture was poured onto water and then made basic with

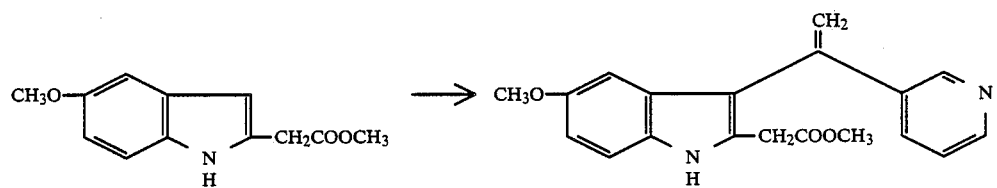

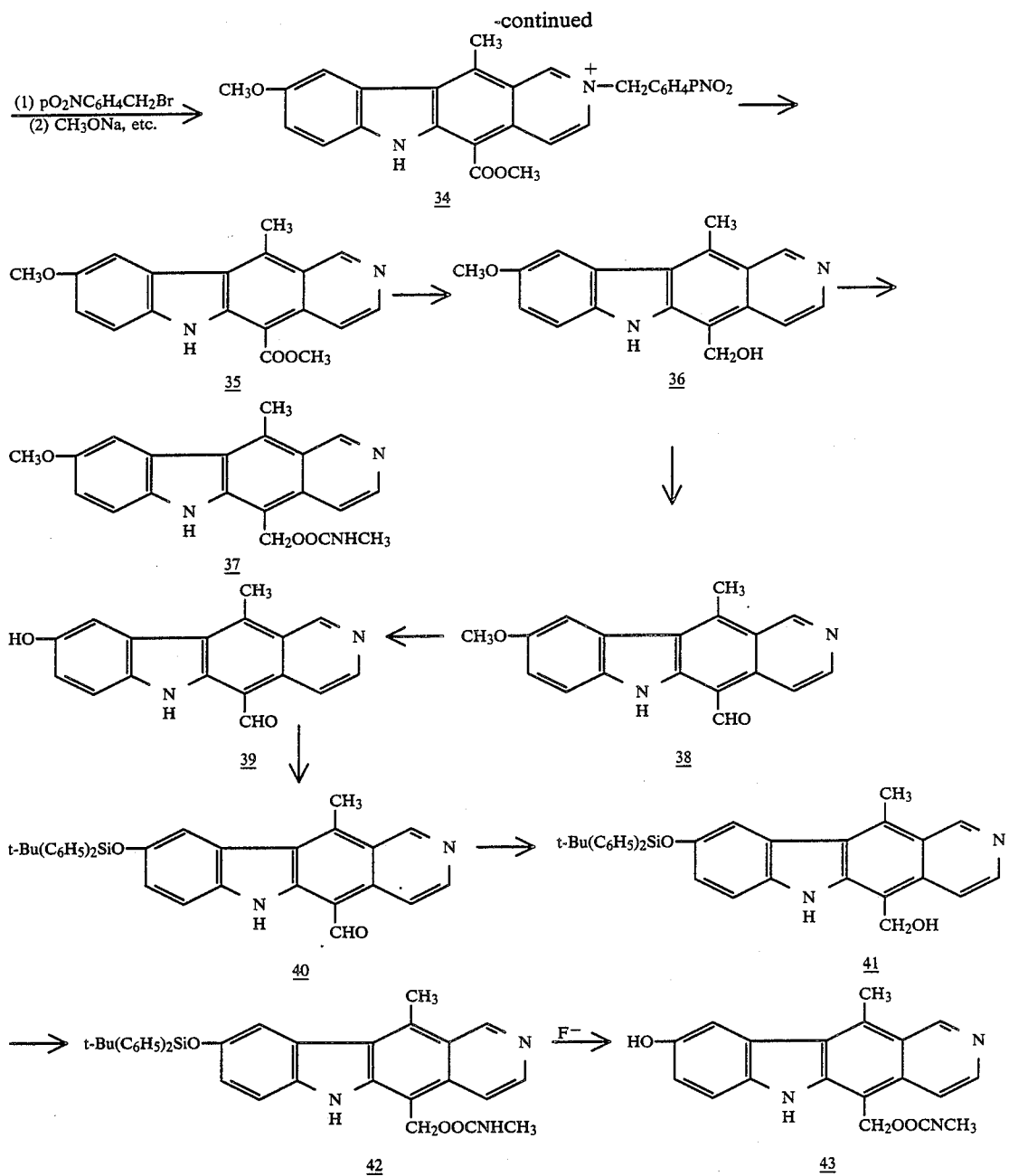

NH$_4$OH. The suspension was extracted with ether and the ether extract was washed with water, dried and evaporated to dryness to leave a brown oil which was triturated with a solution of ether-hexane, whereupon the oil crystallized. The white solid was filtered, washed with hexane and dried m.p. 154°–156° C. (wt. 1.5 g). An analytical sample was obtained by chromatography on silica gel (30% ethyl acetate/methylene chloride, followed by crystallization from aqueous methanol. m.p. 164°–165° C.

9-Methoxy-5-carbomethoxy-11-methyl-6H-pyrido [4,3-b] carbazole (35)

Seven grams of the pyridyl ethene 33 was dissolved in 200 mL of dry acetone and 14.0 g of p. nitrobenzyl bromide was added. The solution was stirred under nitrogen for 48 hours. Ether was added to the suspension which was filtered and washed with dry ether to give 11.64 g of the crude salt 31.

A solution of 11 g of the above quaternary salt was dissolved in 150 mL of dry methanol and 0.7 g of sodium metal (cut into small pieces to facilitate dissolution) was added. When all the sodium had dissolved, ethyl nicotinate methiodide (prepared from 20 g of ethyl nicotinate and 20 mL of methyl iodide in dry acetone) was added and the mixture was stirred at room temperature under nitrogen for 24 hours. At the end of that time the crystals that separated were filtered, washed with fresh methanol and dried to form wt. 9.98 g of the cyclized ether 34.

A suspension of 3.0 g of the quaternary salt 34 in 500 mL of dry methanol was stirred while 400 m of small pieces of sodium metal was added. This was followed by a solution of 1.26 g of p.-nitrosodimethylaniline in 300 mL of dry chloroform. The reaction mixture was stirred under nitrogen for 24 hours. The solvents were removed under reduced pressure at 30°–35° C. and the residue was partitioned between 200 mL of methylene chloride and water. The organic layer was washed with water, dried and evaporated to dryness. The ester was obtained after careful chromatography to remove red by-products. The analytical sample was obtained by crystallization from ethyl acetate. The yellow crystals of 35 melted at 178°–179° C.

9-Methoxy-5-hydroxymethyl-11-methyl-6H-pyrido [4,3-b] carbazole (36)

To a solution of 600 mg of the ester 35 in freshly distilled dry tetrahydrofuran there was added portion wise, 200 mg of lithium aluminum hydride. The reaction mixture was heated under reflux for 2 hours and stirring was continued at room temperature for an additional 2 hours. An additional quantity of 100 mg of lithium aluminum hydride was added. An hour and 30 minutes of stirring at room temperature no more starting ester was detectable by thin layer chromatography.

Ethyl acetate was added to destroy the excess lithium aluminum hydride. Water (5 mL) was added followed by 5 mL of 2N sodium hydroxide. After stirring at room temperature for 30 minutes the mixture was filtered and the solid was washed with tetrahydrofuran followed by methanol-chloroform (1:9). The filtrates were combined and dried over sodium sulfate and taken to dryness. After chromatography of the residue using ethyl acetate followed by methanol/ethyl acetate (1:9) there was obtained 297 mg of the desired alcohol 36 which after crystallization from ethyl acetate melted at 208°–209° C.

9-Methoxy-5-hydroxymenthyl-11-methyl-6H-pyrido [4,3,-b] carbazole-N-methylcarbamate (37)

The above alcohol 36 was dissolved in dry pyridine and dry acetone and treated with methyl isocyanate as in the case of the carbinol 25. The mixture was stirred until no further alcohol 36 could be detected on thin layer chromatography. The solvents were evaporated and the residual solid was crystallized from ethyl acetate-methanol to give the desired carbamate 37.

9-Methoxy-11-methyl-6H-pyrido [4,3-b] carbazole-5-carboxaldehyde (38)

A solution of 250 mg of the hydroxymethyl compound 36 was refluxed in 150 mL of acetone until all was in solution. One gram of manganese dioxide was added. The mixture was refluxed for about 4 hours and was then filtered while still hot. The insoluble material was washed with acetone. The combined acetone filtrates were evaporated to dryness to leave a crystalline residue which after recrystallization from methanol melted at 252°–254° C.

9-Hydroxy-11-methyl-6H-pyrido [4,3-b] carbazole-5-carboxaldehyde (39)

A solution of 1.6 g (0.6 mL) of boron bromide in 5 mL of dry methylene chloride was added dropwise to a stirred suspension of 200 mg of the methoxyaldehyde 38 in 50 mL of dry $CH_2Cl_2$ at $-78°$ C. The stirred suspension was allowed to warm to room temperature and stirred for an additional 6 hours. The mixture was cooled in an ice bath and about 5 mL of ice-water was added after 30 minutes the methylene chloride layer was separated under nitrogen. The aqueous brown suspension was cooled in an ice-bath and made alkaline with 15 mL of 10% sodium hydroxide under nitrogen. The dark red solution was taken to pH 7–8 with the aid of acetic acid, sodium bicarbonate solution. The brown precipitate was collected on a filter, washed with water and dried. The dry solid was triturated with methylene chloride-hexane (1:1) and filtered to give the desired crude phenolic aldehyde. Wt. 170 mg, m.p. 346°–349° C.

9-t-Butyl diphenyl silyloxy-11-methyl-6H-pyrido [4,3-b] carbazole-5-carboxaldehyde (40)

A solution of 106 mg of the phenolic aldehyde 39 and 680 mg of imidazole in 10 mL of dry dimethyl formamide was stirred at 80° C. in a nitrogen atmosphere while 212 microliters of t-butyl diphenylchlorosilane was added. The mixture was stirred at 80° C. for 40 hours, before being cooled and treated with 100 mL of ether. The organic layer was washed with water and the aqueous extract was back extracted with ether. The combined ether extracts were washed with water and then evaporated to dryness to leave a solid which was triturated with hexane to leave 150 mg of the desired product. Evaporation of the hexane filtrate left a solid which after thin layer chromatography gave an additional 28 mg of the desired aldehyde. Total yield 178 mg. After crystallization from ethyl acetate there was obtained 103 mg of pure 40 m.p. 241°–243° C.

9-t-Butyldiphenylsilyloxy-5-hydroxymethyl-11-methyl-6H-pyrido [4,3-b] carbazole (41)

A solution of 115 mg of the aldehyde 38 in 50 mL of ethanol was stirred at room temperature while 50 mg of sodium borohydride was added in one portion. After one hour at room temperature the reaction mixture was poured into water and 5 mL of 5% ammonium chloride solution, stirred for 10 minutes and extracted with methylene chloride. The organic extract was washed with water and taken to dryness to give 116 mg of crude carbinol. Recrystallization from ethanol gave 42 mg of pure 41 m.p. 208°–210° C. An additional 34 mg was obtained from the ethanol mother liquor.

9-Hydroxy-5-hydroxymethyl-11-methyl-6H-purido [4,3-b] carbazole (43)

A solution of 18 mg of the carbinol 41 in 20 mL of dry methylene chloride was stirred while 48 mg of methyl isocyanate and 7 mg of 4-dimethylamino pyridine were added. The reaction mixture was left overnight. The reaction mixture was evaporated to dryness in vacuo and the residue was chromatographed on a preparative thin layer silica gel plate using ethyl acetate-methanol (19/1) as the developing solvent. There was obtained 8 mg of the desired N-methylcarbamate 42 identified by infra-red and NMR spectrum.

The above carbamate was dissolved in dry tetrahydrofuran and stirred in a nitrogen atmosphere while a solution of 1M tetrabutylammonium fluoride in dry tetrahydrofuran as added at 0° C. The solution was allowed to warm to room temperature and after powdered dry ice was added the solvent was removed in vacuo at room temperature. The residue was dissolved in acid-free chloroform and washed with water. The chloroform was dried, evaporated in vacuo at room temperature and triturated with hexane to remove most of the t-butyldiphenylsilyl fluoride leaving the desired carbamate 43.

What is claimed is

1. The compound 9-substituted 5-hydroxymethyl-11-methyl-6H-pyrido [4,3-b] carbazole N-alkyl or aryl carbamates of the structure:

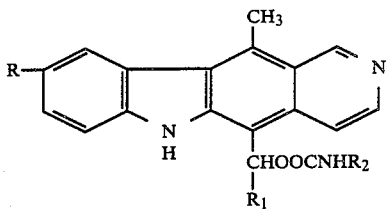

where R=H, lower alkoxy, OH, phenyloxy
 R$_1$=H or lower alkyl
 R$_2$=lower alkyl or phenyl 2. The compound according to claim 1 where the lower alkoxy and lower alkyl radicals have from 1 to 5 carbon atoms.

3. The compound according to claim 1 wherein R=H, R$_1$=H and R$_2$=CH$_3$.

4. The compound according to claim 1 wherein R=CH$_3$O, R$_1$=H, R$_2$=CH$_3$.

5. A method of treating schistosomiasis of mammals comprising applying a clinically active dosage of the compound 9-substituted 5-hydroxy-methyl-11-methyl-6H-pyrido[4,3-b] carbazole N-alkyl or aryl carbamates of the structure:

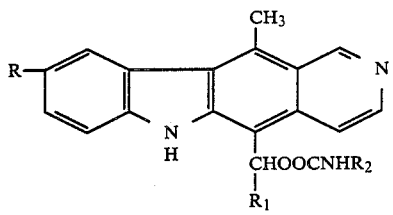

where R=H, lower alkoxy, OH, phenloxy
 R$_1$=H or lower alkyl
 R$_2$=lower alkyl or phenyl to a mammolion host in need thereof.

6. The method according to claim 5 wherein R=methoxy.

7. The method according to claim 5 wherein R=hydrogen.

* * * * *